United States Patent [19]

Seiverd

[11] 4,444,189

[45] Apr. 24, 1984

[54] PHOTOTHERAPY BOOTH

[76] Inventor: Paul J. Seiverd, 550 Arlington Ave., Milmont Park, Pa. 19033

[21] Appl. No.: 333,226

[22] Filed: Dec. 21, 1981

[51] Int. Cl.$^3$ .................... A61M 33/00; A61M 33/06
[52] U.S. Cl. .................................. 128/395; 128/371; 128/396
[58] Field of Search ............... 128/395, 396, 362, 371, 128/372

[56]  References Cited

U.S. PATENT DOCUMENTS

| | | | |
|---|---|---|---|
| D. 248,315 | 6/1978 | Blaisdell et al. | 128/396 |
| D. 249,552 | 9/1978 | Schwartz | 128/396 |
| 1,506,502 | 8/1924 | Rheinberger . | |
| 1,583,420 | 5/1926 | Picard | 128/395 |
| 1,718,970 | 6/1929 | Zublin | 128/396 |
| 2,382,939 | 8/1945 | Koch . | |
| 3,873,219 | 3/1975 | Pofferi | 403/171 |
| 3,986,316 | 10/1976 | Blodee | 52/753 D |
| 3,986,513 | 10/1976 | Stuhl | 128/395 |
| 4,024,686 | 5/1977 | Gronert | 52/282 |
| 4,100,415 | 7/1978 | Blaisdell et al. . | |

OTHER PUBLICATIONS

Documents of National Biological Corp.
Documents of Derma Control, Inc.

Primary Examiner—C. Fred Rosenbaum
Assistant Examiner—C. W. Shedd
Attorney, Agent, or Firm—Seidel, Gonda & Goldhamer

[57]  ABSTRACT

A phototherapy booth is provided with sources of flourescent black light for use by persons suffering from a medical skin disorder. The booth includes at least three walls made from a rigid perforated substrate to facilitate dissipation of heat. At least one lamp on each wall is vertically adjustable along a track for increasing the height of light exposure. The walls may be vertically disposed for use by a person who is ambulatory or may be arranged as a tunnel for use by a person who is bedridden.

9 Claims, 9 Drawing Figures

PHOTOTHERAPY BOOTH

BACKGROUND

Phototherapy booths are known. For example, see U.S. Pat. 4,100,415. Such booths are provided for medical treatment of skin disorders by exposing the skin to flourescent black light with or without prior application of topical drugs. The booth disclosed in said patent is large, heavy, and expensive whereby it does not lend itself to home use. Since lamps are not commercially available in a length exceeding four feet, this presents a problem due to the fact that most people are more than four feet tall. The present invention is directed to a solution of those problems.

SUMMARY OF THE INVENTION

The invention is directed to a phototherapy booth for exposing a person to flourescent black light within a confined space. The space is confined by at least three walls with the first wall extending between a side edge of each of the second and third walls. The walls are releasably coupled together and are made from rigid perforated substrates. Flourescent lamps for emitting black light are attached to each of the walls. At least one lamp on each wall is vertically adjustable along a track for increasing the effective height of light exposure. A switch means is provided on one of the walls for controlling said lamps. Electrical conductor means interconnects the lamps on the first wall to the lamps on the second and third walls.

It is an object of the present invention to provide a novel phototherapy booth which is adapted for home use.

It is another object of the present invention to provide a phototherapy booth which can be knocked down for purposes of storage.

It is another object of the present invention to provide lightweight inexpensive phototherapy booth which is adaptable for use by persons of different heights.

Other objects and advantages of the present invention will appear hereinafter.

For the purpose of illustrating the invention, there is provided in the drawing a form which is presently preferred; it being understood, however, that this invention is not limited to the precise arrangements and instrumentalities shown.

DETAILED DESCRIPTION

Figure 1:
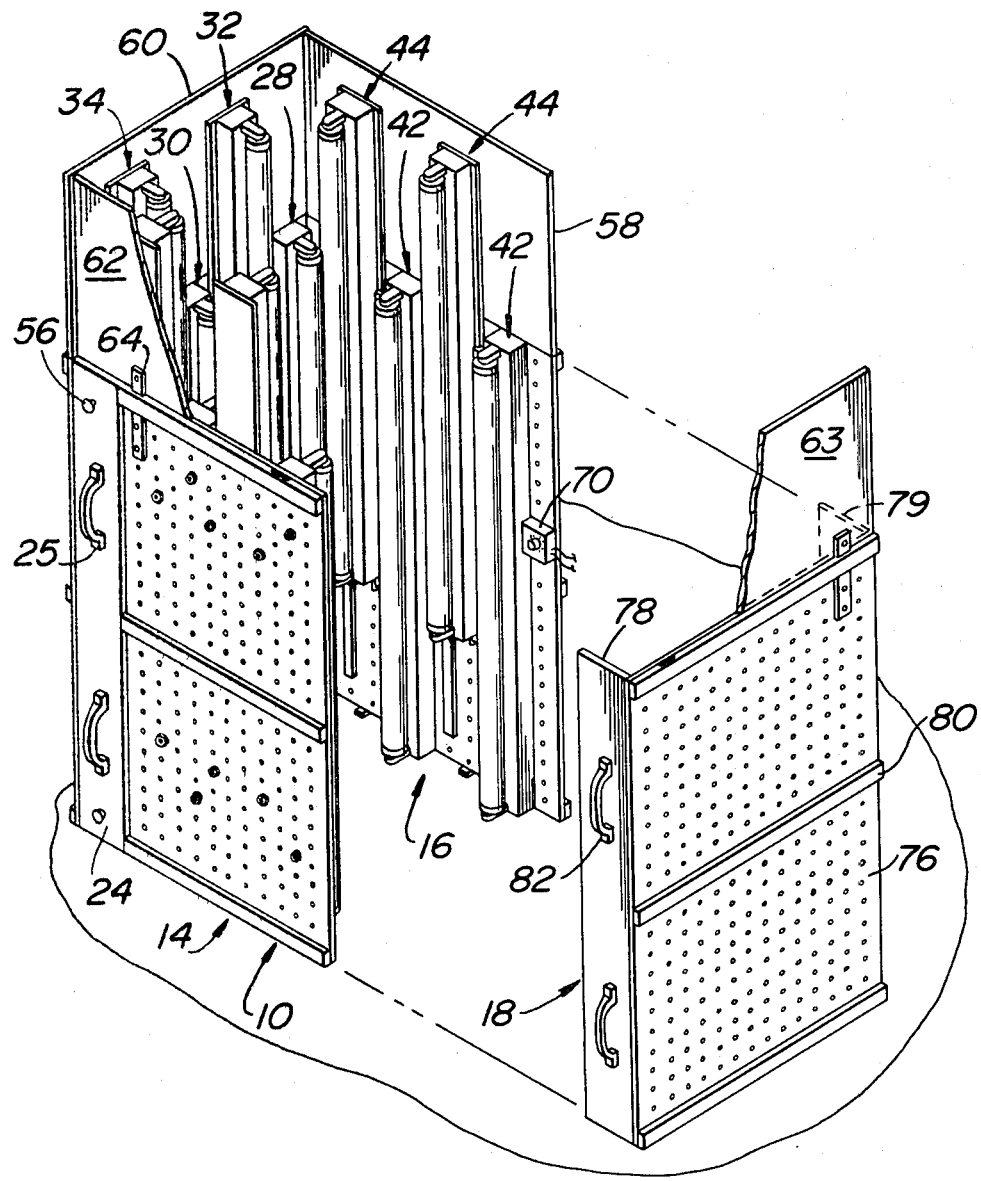
FIG. 1 is a perspective view of a booth in accordance with the present invention.

Referring to the drawings in detail, wherein like numerals indicate like elements, there is shown in FIG. 1 a booth in accordance with the present invention designated generally as 10. The booth 10 is comprised of at least three walls, namely a first wall 12, a second wall 14 and a third wall 16. There is preferably provided a fourth wall 18.

Each of the walls is preferably constructed of the same materials. For purposes of illustration, see FIG. 2 which is an exploded view of the components on the walls. Wall 12 is comprised of a perforated substrate 20 such as tempered peg board with reinforcement strips 22 being applied to render the wall more rigid. Each of the other walls is similarly constructed of a tempered peg board which is similarly reinforced. Peg board is a type of wood composition substrate which is perforated so as to facilitate hanging tools and other devices thereon. For the purposes of the present invention, peg board has been chosen because the perforations will facilitate dissipation of heat.

Figure 2:
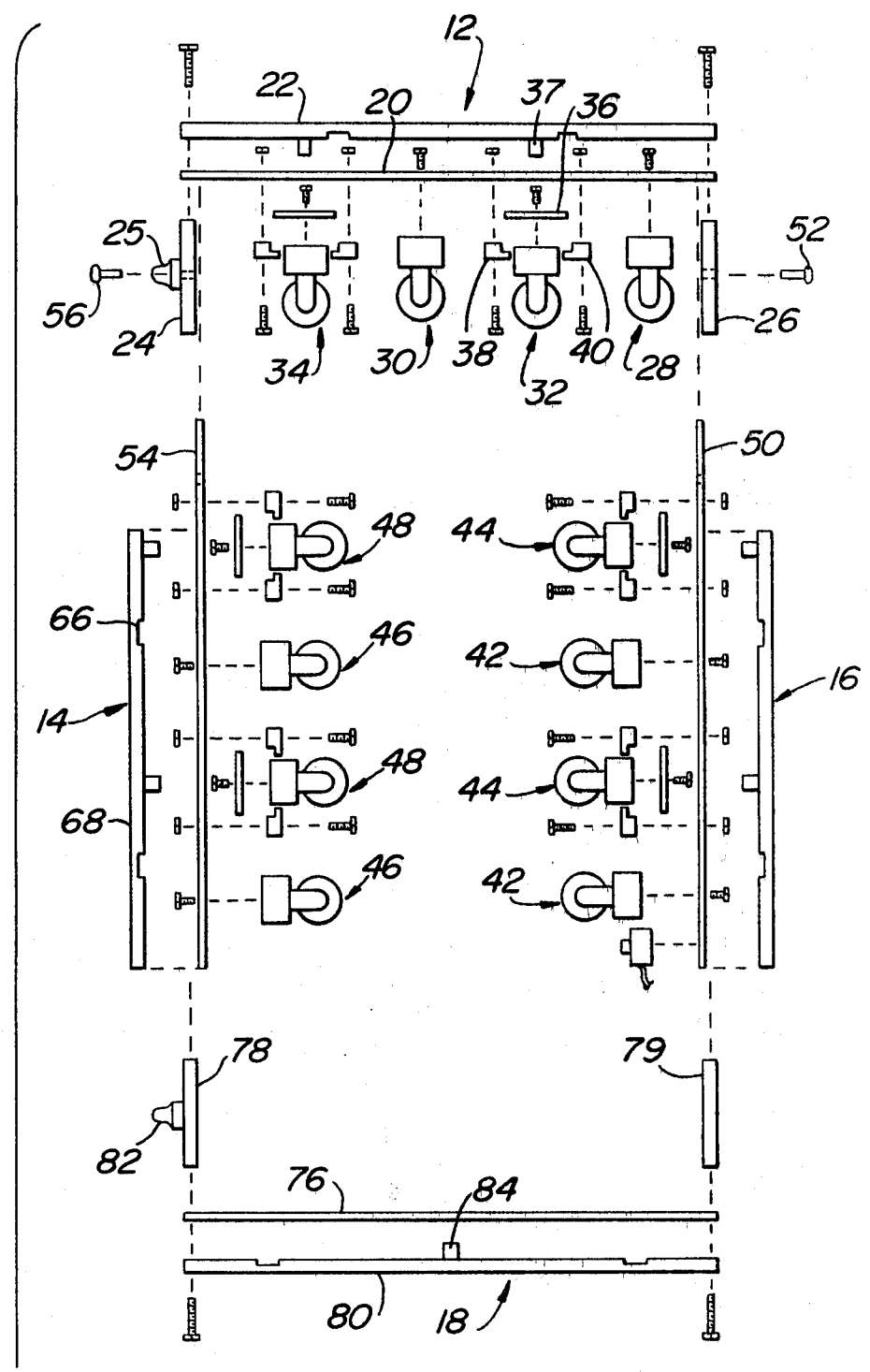
FIG. 2 is a top plan view of the booth in an exploded illustration.
Figure 3:
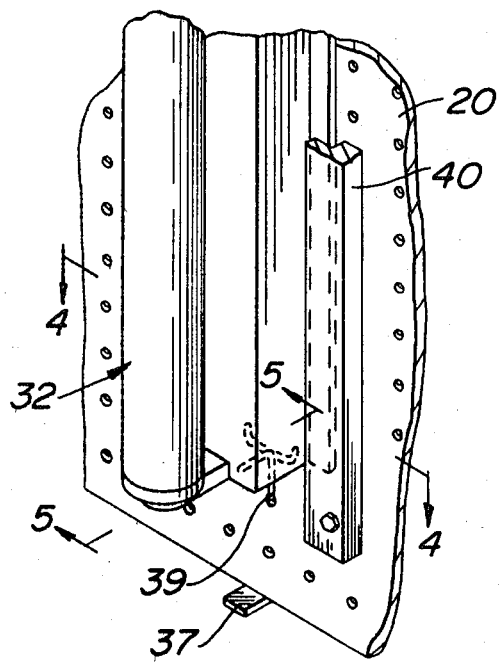
FIG. 3 is a partial perspective view of the lower end of a lamp on the lower end of one of the walls.
Figure 4:
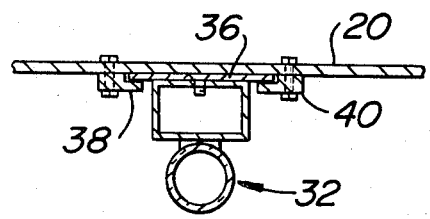
FIG. 4 is a sectional view taken along the line 4—4 in FIG. 3.
Figure 5:
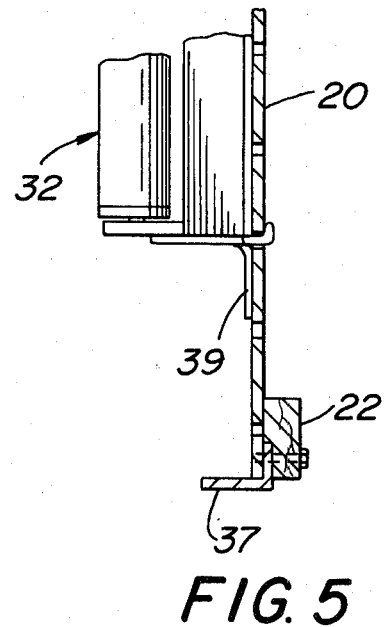
FIG. 5 is a sectional view taken along the lin 5—5 in FIG. 3.

Referring particularly to FIG. 2, the first wall 12 has a pair of stationary lamps 28 and 30 attached thereto by fasteners. Wall 12 also has a pair of adjustable lamps 32 and 34. Lamps 32 and 34 are vertically adjustable to extend the effective range of the lamps depending upon the height of the person whose skin is to be exposed to the ultraviolet black light from the lamps. If desired, the bulb of each lamp may have a protective plastic sleeve to confine distribution of glass pieces if the bulb is broken due to impact. Since all vertically adjustable lamps are identical, only lamp 32 will be described in detail.

Referring to FIGS. 2–5, a spacer 36 is attached to a rear face of the housing of lamp 32. A limit stop 37 is attached to the lower end of the substrate 20 to define the lowermost position of lamp 32 so that it is in line with the other lamps on the same wall. Track members 38 and 40 are provided. Each track member overlaps one longitudinally extending side edge portion of the spacer 36. The track portions are releasably attached to the substrate 20. A removable and adjustably positioned clip 39, as used conventionally in connection with peg boards, is provided to support the lower end of the lamp housing when the lamp 32 is in an elevated position. See FIG. 5.

Wall 16 has a pair of stationary lamps 42 which are identical with lamps 28 and 30. Wall 16 has a pair of vertically adjustable lamps 44 which are identical with lamp 32. Wall 14 is similarly provided with stationary lamps 46 and vertically adjustable lamps 48. Wall 16 has an extension portion 50 along one vertically disposed side edge portion. Extension 50 overlaps a flange 26 on the wall 12 and is releasably coupled thereto by fasteners 52. Fasteners 52 may merely be pins which extends through aligned holes in the flange 26 and extension 50 or may be threaded bolts having a wing nuts. Wall 14 is similarly provided with an extension 54 for cooperation with the flange 24 on the other side edge of wall 12. Similar fasteners extend through aligned holes in the flange 24 in extension 54.

When lamps are vertically adjusted to a position as shown in FIG. 1, to more effectively utilize the light there is preferably provided an extension panel for each of the walls. Thus, wall 16 has an extension panel 58; wall 12 has an extension panel 60; wall 14 has an extension panel 62 and wall 18 has an extension panel 63.

Each of the extension panels is identical. Hence, only extension panel 62 will be described in detail.

Extension panel 62 may be a solid substrate or may be a perforated substrate such as peg board. A pair of brackets 64 is attached to an outer surface of the extension panel 62. Each bracket 62 extends downwardly through a notch 66 on the inner surface of the uppermost reinforcement strip 68. See FIGS. 1 and 2. The bottom edge of panel 62 rests on the upper end of the wall 14. The inner surface of each substrate and each extension panel is preferably a light reflecting surface which may be attained by applying white paint, silver paint, etc. If desired, an aluminum foil may be adhered to the inner surface in each substrate and extension panel. If such aluminum foil is applied, it should be perforated in the same pattern as the peg board substrates. If desired, imperforate aluminum foil may be applied to the substrates and/or panels and thereafter a nail or other tool is utilized to punch a hole in the aluminum foil in the pattern of the holes in the substrates.

Figure 8:
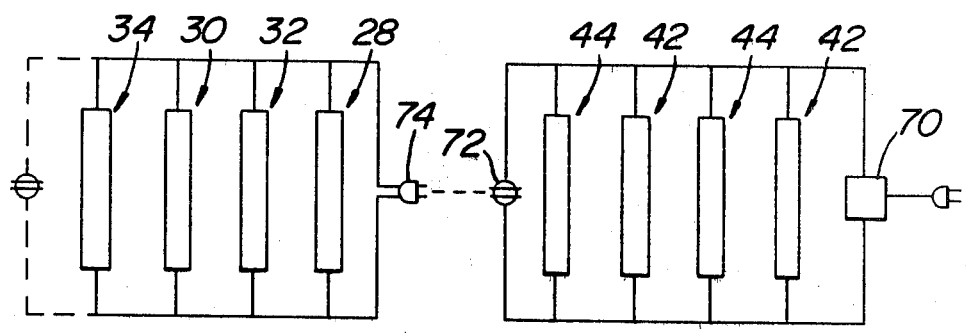
FIG. 8 is a wiring diagram for the lamps on two adjacent walls.

One of the walls such as wall 16 is provided with a timer switch 70. See FIGS. 1 and 8. Timer switch 70 is adapted to be connected to an external source of electrical potential and is coupled to each of the lamps 42, 44 as shown in FIG. 8. In addition, timer switch 70 is coupled to an electrical receptacles 72 on wall 16. An electrical plug 74 on wall 12 is adapted to be releasably coupled to the receptacle 74 so that the lamps 28, 30, 32 and 34 will also be coupled to the timer switch 70. In a similar manner, an electrical plug on wall 14 is releasably connected to an electrical receptacle on wall 12.

Figure 6:
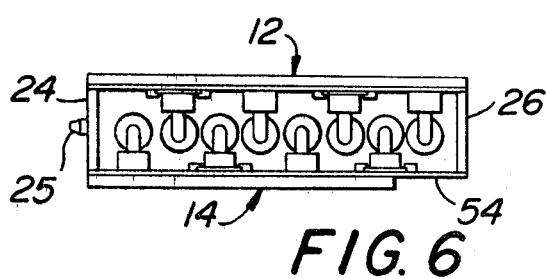
FIG. 6 is an end view showing two walls coupled together for purposes of storage and/or transportation.
Figure 7:
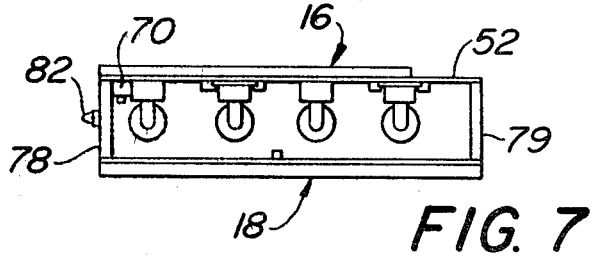
FIG. 7 is an end view showing the other two walls coupled together for storage and/or transportation.

Due to the extension 54 on wall 14, wall 14 and wall 12 may be coupled together for purposes of storage and/or shipment as shown in FIG. 6. Likewise, walls 16 and 18 may be coupled together as shown in FIG. 7. In the storage position of the walls, they may be releasably held together in any convenient manner such as by a strap.

Figure 9:
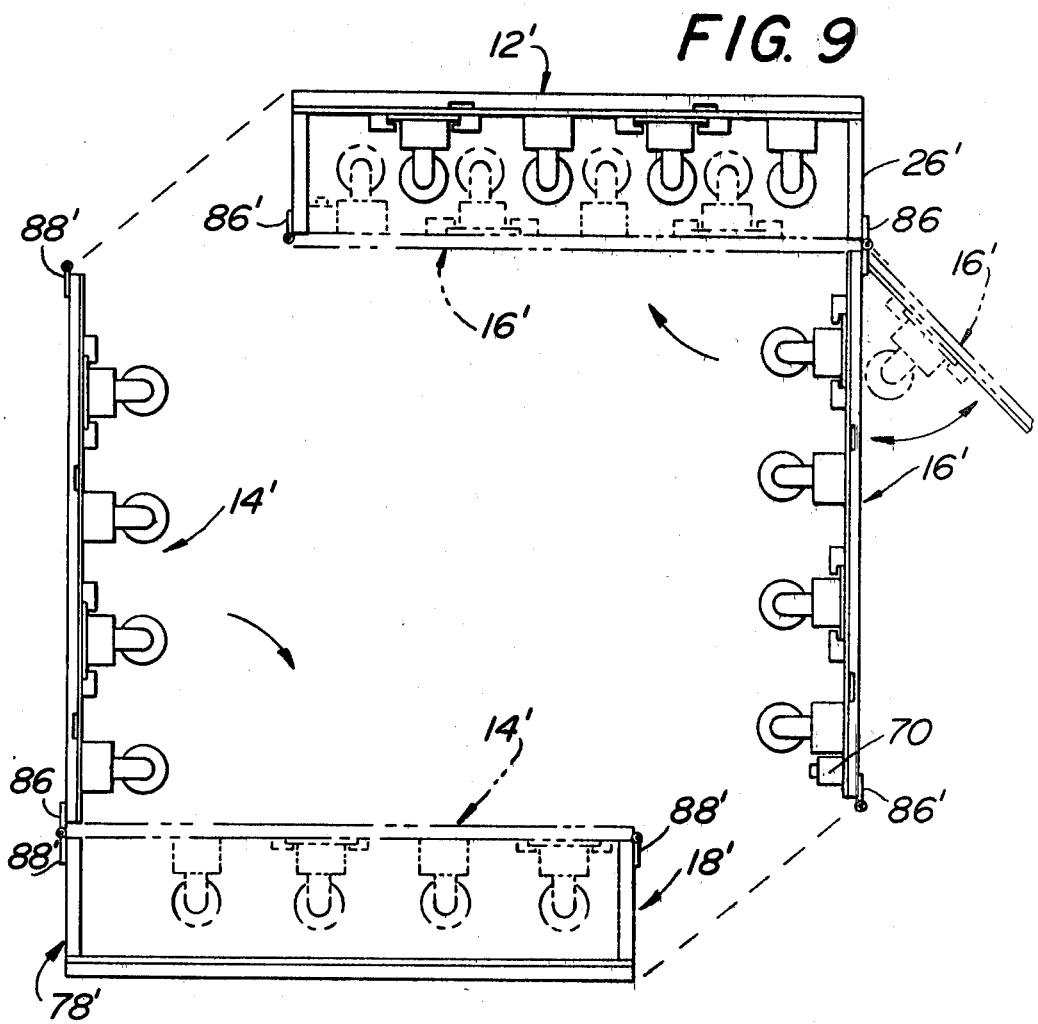
FIG. 9 is an end view showing an alternative manner for coupling the walls together and facilitating knockdown of the walls.

Referring to FIG. 9, there is illustrated another embodiment of the present invention wherein corresponding elements are identified by corresponding primed numerals. As shown in FIG. 9, wall 16' is pivotably connected to the flange 26' on the wall 12' by hinge 86. Wall 14' is connected to flange 78' on wall 18' by way of a hinge 88. The hinges 86 and 88 facilitate pivoting the walls to the position shown in FIG. 9. The free ends of walls 12' and 16' each have one half of a hinge 86' which may be coupled together by a hinge pin. The free ends of walls 14' and 18' are similarly provided with one half of a hinge 88'. Hence, an external strap or the like for retaining the walls in a collapsed position is not needed.

While the illustration in the drawings and the description set forth above is directed to a booth having a minimum of three walls and preferably four walls, the present invention may be structurally interrelated in a manner so as to have more than four walls if desired. The booth 10 is lightweight and constructed of inexpensive materials which are commercially available whereby the booth may be sold for home use. A home use booth in accordance with the present invention is less expensive and more convenient for persons who must have phototherapy to cure skin disorders. While the booth of the present invention is primarily designed for use as a phototherapy booth, it may be utilized for other purposes. The booth may be vertically disposed as shown in FIG. 1 wherein the person will be standing. Alternatively, the booth may be arranged as a tunnel with wall 12 horizontally disposed and supported by the walls 14 and 16 for a person who is bedridden.

The booth 10 is preferably constructed so as to have a height of 4 to 5 feet with the extension panels providing additional height as required whereby persons of different heights may utilize the booth. While the substrates are perforated tempered peg board, they may be perforated aluminum, perforated plastic, etc. The perforated substrates facilitate convection cooling as well as supplying an adequate number of locations for the placement of attachment of reinforcement strips, brackets, and the like. If desired, wall 18 may have straps or handles 84 on the inner surface thereof to facilitate ease of manipulation of the wall 18 particularly when a person is disposed within the booth 10. The handles 25 and 82 facilitate ease of carrying the walls when in the collapsed position as shown in FIGS. 6 and 7.

The present invention may be embodied in other specific forms without departing from the spirit or essential attributes thereof and, accordingly, reference should be made to the appended claims, rather than to the foregoing specification, as indicating the scope of the invention.

I claim:

1. A booth for exposing a person to light within a confined space comprising at least three walls with the first wall extending between a side edge of each of the second and third walls, means coupling said walls together, said walls being rigid perforated substrates, ultraviolet lamps on each of said walls, at least one lamp on each wall being vertically adjustable along a track on its wall for increasing the effective height of light exposure to a person within the booth, switch means on one of said walls for controlling said lamps, and electrical conductor means interconnecting the lamps on said one wall to the lamps on said other walls.

2. A booth in accordance with claim 1 wherein the first wall is perpendicular to said second and third walls, said second and third walls overlapping a portion of said first wall, and at least two lamps on each wall being vertically adjustable.

3. A booth in accordance with claim 2 including a fourth wall lacking lamps and positionable parallel to the first wall so as to complete an enclosure for a person requiring phototherapy.

4. A booth in accordance with claim 1 wherein said perforated substrates are made from reinforced peg board.

5. A booth in accordance with claim 1 wherein one end of the second wall is coupled to the first wall by hinges.

6. A booth in accordance with claim 1 wherein the ends of the first wall have flanges, each flange overlying a portion of the second or third wall with said coupling means including a member extending through the overlapped portions of the walls.

7. A booth for exposing a person to black light for phototherapy within a confined space comprising at least three walls with the first wall extending between a side edge of each of the second and third walls, said first and third walls being perpendicular to said first wall and parallel to each other, each of the second and third walls overlapping a portion of the first wall, said walls being rigid perforated substrates, a discrete extension panel for each wall, mating structure on the lower edge of each panel and the upper end of each wall so that each extension panel may extend the height of its associated wall, the inner surface of each extension panel and wall being a light reflective surface, a plurality of parallel black light lamps attached to each of said walls on an inner surface thereof, switch means on one of said walls for controlling all of said lamps, an electrical conductor means removably interconnecting the lamps on said one wall to the lamps on said other walls.

8. A booth in accordance with claim 7 including means on the walls to facilitate a knock-down of the walls and overlapping arrangement for purposes of storage.

9. A booth in accordance with claim 7 including clips adapted to enter perforations in the substrates for contacting a lower end of the lamps and for temporarily holding some of the lamps in an elevated position projecting above the upper ends of the substrates.

* * * * *